United States Patent
Juergens

(10) Patent No.: US 11,571,175 B2
(45) Date of Patent: Feb. 7, 2023

(54) MOTION CORRECTION METHOD

(71) Applicant: Siemens Healthcare GmbH, Erlangen (DE)

(72) Inventor: Markus Juergens, Adelsdorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 65 days.

(21) Appl. No.: 17/325,605

(22) Filed: May 20, 2021

(65) Prior Publication Data
US 2021/0369221 A1    Dec. 2, 2021

(30) Foreign Application Priority Data
May 28, 2020 (DE) .................. 10 2020 206 729.5

(51) Int. Cl.
*A61B 6/00* (2006.01)
*G01N 23/046* (2018.01)

(52) U.S. Cl.
CPC ............ *A61B 6/481* (2013.01); *A61B 6/4241* (2013.01); *A61B 6/482* (2013.01); *A61B 6/5205* (2013.01); *G01N 23/046* (2013.01)

(58) Field of Classification Search
CPC ....... A61B 6/481; A61B 6/4241; A61B 6/482; A61B 6/5205; A61B 6/032; A61B 6/5264; G01N 23/046
See application file for complete search history.

(56) References Cited

U.S. PATENT DOCUMENTS

| | | |
|---|---|---|
| 7,778,454 B2 | 8/2010 | Grasruck et al. |
| 2011/0097273 A1 | 4/2011 | Proksa |

(Continued)

FOREIGN PATENT DOCUMENTS

| | | |
|---|---|---|
| DE | 102006009222 A1 | 9/2007 |
| DE | 102018204093 A1 | 9/2019 |

OTHER PUBLICATIONS

Faby, Sebastian et al. "Performance of today's dual energy CT and future multi energy CT in virtual non-contrast imaging and in iodine quantification: A simulation study" Medical Physics, vol. 42, No. 7, pp. 4349-4366, Jul. 2015 // DOI: 10.1118/1.4922654.

(Continued)

*Primary Examiner* — Courtney D Thomas
(74) *Attorney, Agent, or Firm* — Harness, Dickey & Pierce, P.L.C.

(57) ABSTRACT

In an embodiment of a motion correction method, a first virtual non-contrast X-ray image of a region under examination is determined based upon first spectral raw X-ray data associated with a first contrast distribution, via material decomposition. In addition, a second virtual non-contrast X-ray image of the region under examination is determined based upon second spectral raw X-ray data associated with a second contrast distribution, differing from the first contrast distribution, via material decomposition. Then the first virtual non-contrast X-ray image is registered with the second virtual non-contrast X-ray image to determine a transformation field between the two virtual non-contrast X-ray images. Finally, based upon the determined transformation field, first X-ray image data based on the first raw X-ray data is registered with second X-ray image data based on the second raw X-ray data. An X-ray imaging method, a motion correction device and an X-ray imaging system are also discussed.

20 Claims, 3 Drawing Sheets

(56) References Cited

U.S. PATENT DOCUMENTS

2018/0276853 A1* 9/2018 Carmi .................... A61B 6/03
2019/0282184 A1   9/2019 Fournie et al.

OTHER PUBLICATIONS

German Office Action for DE 102020206729.5 dated Mar. 3, 2021.
McCoulough et al.: "Principles and Applications of Multi-Energy CT", Report of AAPM Task Group 291; Mar. 25, 2020.

* cited by examiner

MOTION CORRECTION METHOD

PRIORITY STATEMENT

The present application hereby claims priority under 35 U.S.C. § 119 to German patent application number DE 102020206729.5 filed May 28, 2020, the entire contents of which are hereby incorporated herein by reference.

FIELD

Example embodiments of the invention generally relate to a motion correction method; an X-ray imaging method; a motion correction device; and an X-ray imaging system.

BACKGROUND

Two-dimensional or three-dimensional image data that can be used for visualizing an imaged subject under examination as well as for other applications is commonly generated by modern imaging techniques.

The imaging techniques are often based on detecting X-ray radiation, with projection measurement data, as it is known, being generated. For example, projection measurement data can be acquired using a computed tomography system (CT system).

An X-ray image acquisition often involves using contrast agents, with which the patient is injected in order to increase the contrast of the image acquisition and hence simplify diagnosis. An example of using contrast agents is depicting vessels by X-ray techniques. These X-ray techniques can be performed using conventional systems, C-arm systems, angiography systems or CT systems. Iodine is conventionally used as the X-ray contrast agent in this type of imaging. If the intention now is to visualize different types of tissue of one and the same patient, then it can be useful to generate a plurality of X-ray image acquisitions for a patient using different contrast agents or different contrast-agent concentrations.

The time lag between the different acquisitions, however, causes registration problems because of patient movements. These problems are amplified in particular by the fact that different contrast agents lead to different absolute CT values for the same regions, and also the relative differences in the CT values vary between different regions. The problems with registration arise in particular when different contrast-agent concentrations occur during perfusion acquisitions, multiphase acquisitions and follow-up acquisitions. In these cases, the image impression varies as a result of the contrast agent dynamics as a function of time and as a result of physiological changes. For example, contrast agent accumulates over time in a tumor before treatment, but no longer does so after successful treatment.

It is conventional to use motion correction algorithms in which distance measurements are applied that are, in principle, insensitive to absolute CT values. For example, normalized mutual information (NMI) or the local cross-correlation is used. When using normalized mutual information NMI, the pixel values are interpreted as random variables. The mutual information MI of two images X and Y is then $MI(X;Y)=H(X)-H(X;Y)$, where H is the entropy. Put simply, it states how much uncertainty over X remains if Y is known. The normalized mutual information is then $$NMI=(H(X)+H(Y))/H(X;Y).$$

SUMMARY

In addition, landmark detection can also be used to initialize a motion field. The inventors have discovered that landmark detection must be robust to changes in the concentration of the contrast agents used, however.

The inventors have discovered that a problem therefore exists of how to achieve exact X-ray image acquisitions having different contrast-agent concentrations of one and the same region.

Embodiments of the present application are directed to a motion correction method, an X-ray imaging method, a motion correction device, and an X-ray imaging system.

The manner of embodiments of the invention is described below with reference to the methods, to the motion correction device, to the X-ray imaging system and to the computer program. Features, advantages or alternative embodiments mentioned in this connection can also be applied equally to the other claimed subject matter, and vice versa. In other words, the object-based claims (which claims are directed at the motion correction device, for example) can also be developed by combining with features described or claimed in connection with a method, and vice versa. The corresponding functional features of the method are embodied in this case by corresponding physical modules or subunits of the motion correction device, of the X-ray imaging system or of the computer program.

In the motion correction method according to an embodiment of the invention, a first virtual non-contrast X-ray image is generated. The first virtual non-contrast X-ray image is determined on the basis of first spectral raw X-ray data by way of material decomposition. The first spectral raw X-ray data was acquired from a region under examination and is associated with a first contrast distribution or acquired with this contrast distribution. In addition, a second virtual non-contrast X-ray image is generated from the same region under examination. In this case, the second virtual non-contrast X-ray image is generated or determined on the basis of second spectral raw X-ray data from the region under examination by way of material decomposition. The second spectral raw X-ray data is associated, or acquired, with a second contrast-agent distribution, which differs from the first contrast-agent distribution.

In the X-ray imaging method according to an embodiment of the invention, a first spectral X-ray acquisition of a region under examination is captured with a first contrast distribution. In addition, a second spectral X-ray acquisition of the region under examination is captured with a second contrast distribution. Then the motion correction method according to an embodiment of the invention is used to perform motion correction on the captured acquisitions. Finally, mutually registered first and second image data is generated on the basis of the performed motion correction. The X-ray imaging method according to an embodiment of the invention shares the advantages of the motion correction method according to an embodiment of the invention.

The motion correction device according to an embodiment of the invention has a decomposition unit for determining a first virtual non-contrast X-ray image and a second virtual non-contrast X-ray image. As already described in connection with the motion correction method according to an embodiment of the invention, the first virtual non-contrast X-ray image is obtained on the basis of first raw X-ray data, which is associated with a first contrast distribution, by way of material decomposition. The second virtual non-contrast X-ray image is in turn generated on the basis of second raw X-ray data, which is associated with a second contrast distribution, by way of material decomposition.

A registration unit for registering the first virtual non-contrast X-ray image with the second virtual non-contrast X-ray image is also part of the motion correction device according to the invention. The registration unit is also used to determine a transformation field on the basis of the registration. The aforementioned registration unit is also designed to use the determined transformation field to register first X-ray image data, which is based on the first raw X-ray data, with second X-ray image data, which is based on the second raw X-ray data. The motion correction device according to an embodiment of the invention shares the advantages of the motion correction method according to an embodiment of the invention.

The X-ray imaging system, preferably a CT imaging system, according to an embodiment of the invention has the motion correction device according to an embodiment of the invention. The X-ray imaging system according to an embodiment of the invention shares the advantages of the X-ray imaging method according to an embodiment of the invention.

Most of the essential components of the motion correction device according to the invention can be in the form of software components. This applies in particular to the decomposition unit, the registration unit and the field determination unit of the motion correction device according to an embodiment of the invention. In principle, however, some of these components can also be implemented in the form of software-aided hardware, for instance FPGAs or the like, in particular when especially fast calculations are needed. Likewise, the required interfaces can be designed as software interfaces, for instance if all that is involved is a transfer of data from other software components. They can also be designed, however, as hardware-built interfaces driven by suitable software.

An implementation largely in software has the advantage that even medical imaging systems and/or image reconstruction devices already in use can be easily upgraded by a software update in order to work in the manner according to an embodiment of the invention. In this respect, the object is also achieved by a corresponding computer program product comprising a computer program, which can be loaded directly into a memory device of an X-ray imaging system and which contains program segments in order to perform the software-implementable steps of the method according to an embodiment of the invention when the program is executed in the X-ray imaging system. The computer program product may comprise in addition to the computer program, if applicable, extra elements such as e.g. documentation and/or extra components, including hardware components, such as e.g. hardware keys (dongles etc.) for using the software.

For transfer to the subsystem and/or for storage on, or in, this subsystem, a computer-readable medium, for instance a memory stick, a hard disk or any other portable or permanently installed data storage medium can be used, on which are stored the program segments of the computer program, which program segments can be read and executed by a processing unit. For this purpose, the processing unit can have, for example, one or more interacting microprocessors or the like. For example, the processing unit may be part of a terminal or a controller of an imaging system, for instance of a CT system, although it may also be part of a remotely located server system within a data communication network that communicates with the imaging system.

Another embodiment of the invention is directed to a motion correction method, comprising:
    determining, by way of material decomposition, a first virtual non-contrast X-ray image of a region under examination based upon first spectral raw X-ray data associated with a first contrast distribution;
    determining, by way of material decomposition, a second virtual non-contrast X-ray image of the region under examination based upon second spectral raw X-ray data associated with a second contrast distribution, the second contrast distribution differing from the first contrast distribution;
    registering the first virtual non-contrast X-ray image with the second virtual non-contrast X-ray image, to determine a transformation field between the two virtual non-contrast X-ray images; and
    registering, based upon the transformation field determined, first X-ray image data based on the first raw X-ray data with second X-ray image data based on the second raw X-ray data.

Another embodiment of the invention is directed to a motion correction device, comprising:
    a decomposition device to determine, via material decomposition, a first virtual non-contrast X-ray image based upon first raw X-ray data associated with a first contrast distribution, and to determine, via material decomposition, a second virtual non-contrast X-ray image based upon second raw X-ray data associated with a second contrast distribution; and
    a registration device to determine a transformation field by registering the first virtual non-contrast X-ray image with the second virtual non-contrast X-ray image, and, using the transformation field determined, to register first X-ray image data based on the first raw X-ray data, with second X-ray image data based on the second raw X-ray data.

Another embodiment of the invention is directed to a motion correction device, comprising:
    at least one processor to
    determine, via material decomposition, a first virtual non-contrast X-ray image based upon first raw X-ray data associated with a first contrast distribution,
    determine, via material decomposition, a second virtual non-contrast X-ray image based upon second raw X-ray data associated with a second contrast distribution,
    determine a transformation field by registering the first virtual non-contrast X-ray image with the second virtual non-contrast X-ray image, and
    register, using the transformation field determined, first X-ray image data based on the first raw X-ray data, with second X-ray image data based on the second raw X-ray data.

Another embodiment of the invention is directed to a non-transitory computer program product storing a computer program, directly loadable into a storage device of an X-ray imaging system, including program segments to perform the method of an embodiment when the computer program is executed in the X-ray imaging system.

Another embodiment of the invention is directed to a non-transitory computer-readable medium storing program segments, readable and executable by a processor to perform the method of an embodiment when the program segments are executed by the processor.

BRIEF DESCRIPTION OF THE DRAWINGS

The invention is described again below in greater detail using example embodiments and with reference to the accompanying figures, in which.

DETAILED DESCRIPTION OF THE EXAMPLE EMBODIMENTS

Figure 1:
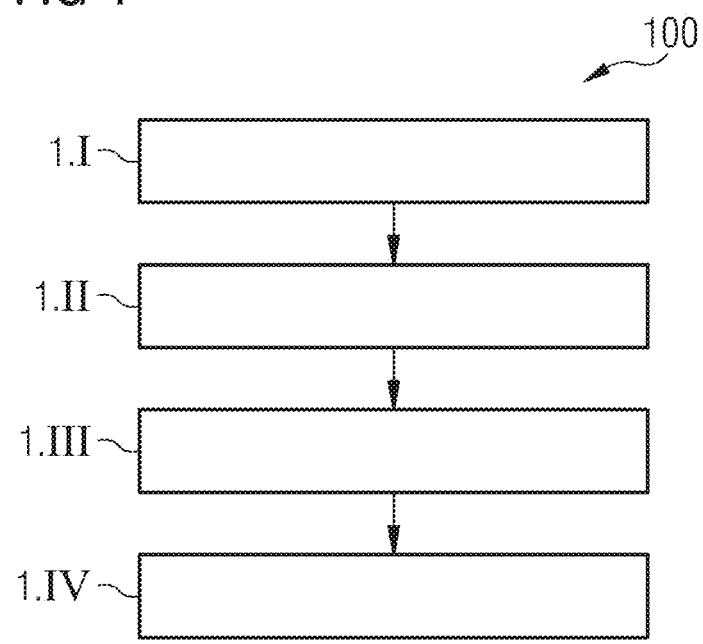
FIG. 1 shows a flow diagram illustrating a motion correction method according to an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In the motion correction method according to an embodiment of the invention, a first virtual non-contrast X-ray image is generated. The first virtual non-contrast X-ray image is determined on the basis of first spectral raw X-ray data by way of material decomposition. The first spectral raw X-ray data was acquired from a region under examination and is associated with a first contrast distribution or acquired with this contrast distribution. In addition, a second virtual non-contrast X-ray image is generated from the same region under examination. In this case, the second virtual non-contrast X-ray image is generated or determined on the basis of second spectral raw X-ray data from the region under examination by way of material decomposition. The second spectral raw X-ray data is associated, or acquired, with a second contrast-agent distribution, which differs from the first contrast-agent distribution.

U.S. Pat. No. 7,778,454 B2, for example, describes a computation method for determining virtual non-contrast X-ray images. McCoulough et al, "Principles and Applications of Multi-energy CT", Report of AAPM Task Group 291, also describes computing virtual mono-energetic image data on the basis of dual-energy and multi-energy CT acquisitions, the entire contents of each of which are hereby incorporated herein by reference. A non-contrast X-ray image shall be understood to mean an X-ray image which was acquired without contrast agent, or in which the contrast is unaffected by a contrast agent. It should be mentioned explicitly in this connection that one or more of the acquisitions of raw X-ray data, for instance the first acquisition, can be performed both with and without contrast agent. Therefore a reference to a contrast distribution may also relate to a real non-contrast image.

A virtual X-ray image shall be understood to mean an X-ray image that has been computed by way of material decomposition. A virtual non-contrast X-ray image shall be understood to mean a non-contrast X-ray image that has been computed on the basis of material decomposition in effectively a "synthetic" manner. Spectral raw X-ray data shall be understood to mean raw X-ray data that has been captured at least using two different X-ray spectra or spectral X-ray components. Typical techniques for obtaining spectral raw X-ray data are multi-energy X-ray acquisitions, dual-energy X-ray acquisitions, and spectral or spectrally resolved X-ray acquisitions by photon-counting detection.

Then the first virtual non-contrast X-ray image is registered with the second virtual non-contrast X-ray image. Registration shall be understood to mean image registration in which a plurality of images are aligned with one another in the best possible way. An equalizing transformation is computed in order to fit the two images to each other. The two images differ from each other because they were acquired at different times. For example, the patient being examined has moved between the two times at which the image of the same region having different contrast distributions was acquired, or individual organs have moved or changed in terms of their condition.

In addition, a transformation field, for instance a displacement field, is determined on the basis of the registration of the virtual non-contrast X-ray images. Finally, first X-ray image data, which is based on the first raw X-ray data, is registered with second X-ray image data, which is based on the second raw X-ray data, on the basis of the determined transformation field, for instance a displacement field. The transformation field is advantageously determined from image data that has the same contrast behavior. This makes it easier to relate individual regions and segments to one another than is the case for image data for which the contrast is different.

In the X-ray imaging method according to an embodiment of the invention, a first spectral X-ray acquisition of a region under examination is captured with a first contrast distribution. In addition, a second spectral X-ray acquisition of the region under examination is captured with a second contrast distribution. Then the motion correction method according to an embodiment of the invention is used to perform motion correction on the captured acquisitions. Finally, mutually registered first and second image data is generated on the basis of the performed motion correction. The X-ray imaging method according to an embodiment of the invention shares the advantages of the motion correction method according to an embodiment of the invention.

The motion correction device according to an embodiment of the invention has a decomposition unit for determining a first virtual non-contrast X-ray image and a second virtual non-contrast X-ray image. As already described in connection with the motion correction method according to an embodiment of the invention, the first virtual non-contrast X-ray image is obtained on the basis of first raw X-ray data, which is associated with a first contrast distribution, by way of material decomposition. The second virtual non-contrast X-ray image is in turn generated on the basis of second raw X-ray data, which is associated with a second contrast distribution, by way of material decomposition.

A registration unit for registering the first virtual non-contrast X-ray image with the second virtual non-contrast X-ray image is also part of the motion correction device according to the invention. The registration unit is also used to determine a transformation field on the basis of the registration. The aforementioned registration unit is also designed to use the determined transformation field to register first X-ray image data, which is based on the first raw X-ray data, with second X-ray image data, which is based on the second raw X-ray data. The motion correction device according to an embodiment of the invention shares the advantages of the motion correction method according to an embodiment of the invention.

The X-ray imaging system, preferably a CT imaging system, according to an embodiment of the invention has the motion correction device according to an embodiment of the invention. The X-ray imaging system according to an embodiment of the invention shares the advantages of the X-ray imaging method according to an embodiment of the invention.

Most of the essential components of the motion correction device according to the invention can be in the form of software components. This applies in particular to the decomposition unit, the registration unit and the field determination unit of the motion correction device according to an embodiment of the invention. In principle, however, some of these components can also be implemented in the form of software-aided hardware, for instance FPGAs or the like, in particular when especially fast calculations are needed. Likewise, the required interfaces can be designed as software interfaces, for instance if all that is involved is a transfer of data from other software components. They can also be designed, however, as hardware-built interfaces driven by suitable software.

An implementation largely in software has the advantage that even medical imaging systems and/or image reconstruction devices already in use can be easily upgraded by a software update in order to work in the manner according to an embodiment of the invention. In this respect, the object is also achieved by a corresponding computer program product comprising a computer program, which can be loaded directly into a memory device of an X-ray imaging system and which contains program segments in order to perform the software-implementable steps of the method according to an embodiment of the invention when the program is executed in the X-ray imaging system. The computer program product may comprise in addition to the computer program, if applicable, extra elements such as e.g. documentation and/or extra components, including hardware components, such as e.g. hardware keys (dongles etc.) for using the software.

For transfer to the subsystem and/or for storage on, or in, this subsystem, a computer-readable medium, for instance a memory stick, a hard disk or any other portable or permanently installed data storage medium can be used, on which are stored the program segments of the computer program, which program segments can be read and executed by a processing unit. For this purpose, the processing unit can have, for example, one or more interacting microprocessors or the like. For example, the processing unit may be part of a terminal or a controller of an imaging system, for instance of a CT system, although it may also be part of a remotely located server system within a data communication network that communicates with the imaging system.

The claims and the following description each contain particularly advantageous embodiments and developments of the invention. In particular, the claims in one category of claims can also be developed in a similar way to the dependent claims in another category of claims. Furthermore, within the scope of the invention, the various features of different example embodiments and claims can also be combined to create new example embodiments.

In one variant of the motion correction method according to an embodiment of the invention, the first contrast distribution differs from the second contrast distribution because of a different contrast-agent concentration distribution. A different contrast-agent concentration distribution may arise, for instance, as a result of the variation over time of a contrast-agent curve at a specific location in the body. Advantageously, despite the image differences caused by the different contrast-agent concentrations of the different images, by using the non-contrast images for determining the transformation for the registration it is possible to relate the same image regions and segments correctly to one another.

In another embodiment of the motion correction method according to the invention, the first contrast distribution differs from the second contrast distribution because different contrast agents are used for the first X-ray image and the second X-ray image. For example, iodine can be used as the contrast agent to depict vessels and soft tissue, barium can be used as the contrast agent to depict the bowel and the abdominal area, and xenon can be used as the contrast agent to depict the lungs and the brain. In order to obtain an overall image of a plurality of different structures, it can be practical to register the two images with one another.

In an alternative embodiment of the motion correction method according to the invention, the method of the sum of squared differences is used for the registration.

This particularly simple and less time-consuming method cannot normally be used for registering different images that have very different contrasts. In the motion correction method according to an embodiment of the invention, however, the transformation between the images is determined on the basis of virtual non-contrast images with the same contrast distribution, and therefore it is possible according to an embodiment of the invention to employ this simple method.

In a particularly advantageous embodiment of the X-ray imaging method according to the invention, the spectral X-ray data is obtained on the basis of one of the following imaging techniques:
photon-counting detection;
dual-source CT;
rapid kV-switching CT;
dual-layer CT;
sequential acquisitions using different X-ray tube voltages;
split-filter CT.

Photon-counting detection allows spectrally resolved capture of raw X-ray data.

In dual-source CT, image acquisitions of one and the same region under examination are performed using at least two different average X-ray energies.

Rapid kV-switching CT involves switching the X-ray source between different X-ray energies, so that a plurality of image acquisitions can be performed likewise simultaneously using different X-ray energies.

In dual-layer CT, the detector consists of two or more layers, each of which detects just part of the X-ray spectrum.

In sequential acquisitions using a different voltage, the same acquisition is performed twice in quick succession, with the X-ray energy being switched between the acquisitions.

In split-filter CT, two different filters, for instance gold and tin, split the X-ray beam longitudinally into two regions, one with a lower spectrum and one with a higher spectrum. Thus in the case of multirow CT, half of the rows detect the low-spectrum signal and the other half detect the high-spectrum signal.

FIG. 1 shows a flow diagram illustrating a motion correction method according to an example embodiment of the invention. The objective of the method is to register two images with one another that were acquired at different times from one and the same region under examination with different contrast distributions, with the aim of correcting movements by the patient. The different contrasts can arise, for example, as a result of the patient having been injected with a contrast agent at a first time t1. A first image of the region under examination was then acquired at a second time t2. At the second time instant, there was a concentration K1 of the contrast agent in the region under examination, which contributes to a first image contrast KT1. Later, a second image acquisition of the region under examination was then generated at a third time t3, for which a second concentration K2 of the contrast agent prevailed that differed from the first concentration at the second time t2. The change in the concentration of the contrast agent used results simply from the fact that the contrast agent flows through the patient's body with the patient's blood flow, and therefore the concentration of the contrast agent varies at different times in one and the same region under examination. The X-ray images produced with different contrast-agent concentrations can then be registered directly with one another only with difficulty because the different contrast complicates segmentation, or generally the spatial association of anatomic structures. Therefore, spectral raw X-ray data is obtained for the X-ray image acquisitions from the region under examination. In other words, at least two spectral components of the X-ray radiation attenuated by the region under examination are detected separately.

The spectrally resolved capture of the raw X-ray data now makes it possible, as part of the motion correction method in step 1.I, to generate by way of material decomposition a first virtual non-contrast X-ray image of the region under examination on the basis of the first spectral raw X-ray data, which was obtained at time t2. This material decomposition involves decomposition of the captured X-ray spectrum into at least two materials, for instance calcium and water, or rather into the X-ray spectra associated with these materials. An image having any X-ray spectrum can now be constructed on the basis of this decomposition. If, in constructing an image, a spectral region is now selected in which the contrast agent has absolutely no effect, which is the case, for instance, far away from the "X-ray edge" of the contrast agent, then what is known as a virtual non-contrast image is generated, which depicts the region under examination at time t2 as though no contrast agent K had been used.

Then, analogous to this procedure, in step 1.II a second virtual non-contrast X-ray image of the region under examination is generated on the basis of the second spectral raw X-ray data obtained at time t3. This process is again performed by way of material decomposition of the second spectral raw X-ray data.

In step 1.III, the two virtual non-contrast X-ray images are then registered with each another. The registration of the two non-contrast X-ray images is now significantly more reliable than registration of image data differently affected by contrast agent because they each have the same image contrast, and therefore the attenuation values of the anatomically important structures in the image representation do not depend on a contrast-agent distribution. The fact that the attenuation values do not depend on the contrast-agent distribution prevents incorrect values for the distance measure of the registration, in particular for the normalized mutual information, the local cross-correlation and the sum of the squared differences, arising in the registration. In other words, the distance measure is dominated by the actual spatial displacements between the two image acquisitions.

In step 1.III, i.e. in the registration, a transformation field is determined. The transformation field provides information on how the two non-contrast X-ray images must be translated, skewed and rotated so that, expressed simply, these images can be made to coincide.

This transformation field is finally applied in step 1.IV to X-ray image data that has been affected by contrast agent and was reconstructed on the basis of the first and second spectral raw X-ray data. Any patient movement between times t2 and t3 is thereby reliably corrected.

Figure 2:
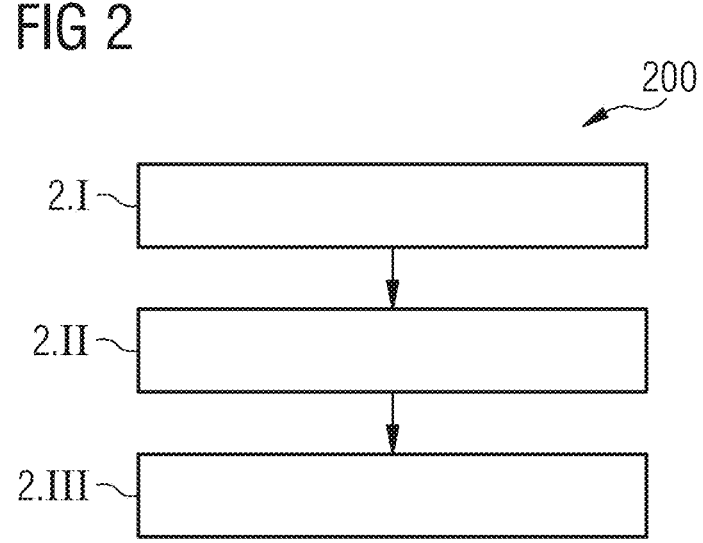
FIG. 2 shows a flow diagram illustrating an X-ray imaging method according to an example embodiment of the invention.

FIG. 2 shows a flow diagram illustrating an X-ray imaging method according to an example embodiment of the invention. First, in step 2.I, a first spectral X-ray acquisition of a region under examination is performed at a time t2, at which a contrast agent is already flowing through the region under examination. In addition, in step 2.II, a second spectral X-ray acquisition of the region under examination is performed at another time t3, at which a different contrast-agent concentration distribution occurs in the region under examination than at time t2. Finally, in step 2.III, the motion correction method according to the invention illustrated in FIG. 1 is applied.

Figure 3:
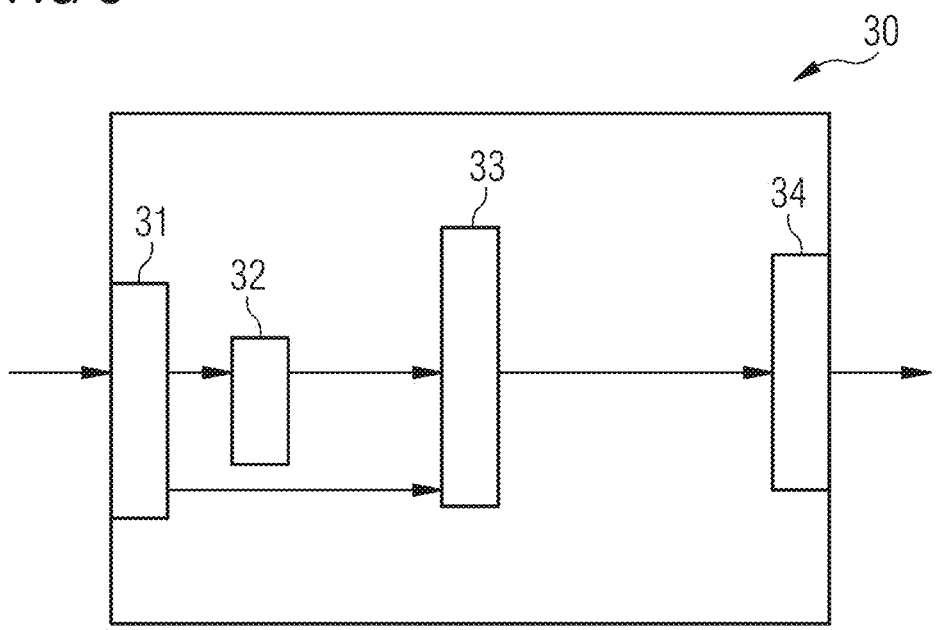
FIG. 3 shows a schematic diagram of a motion correction device according to an example embodiment of the invention.

FIG. 3 shows a schematic diagram of a motion correction device 30 according to an example embodiment of the invention. The motion correction device 30 comprises an input interface 31. The input interface 31 receives spectral raw X-ray data that was captured with different contrast. The raw X-ray data is transferred to a decomposition unit 32, which is designed to generate, by way of material decomposition, a first virtual non-contrast X-ray image on the basis of the first raw X-ray data, which is associated with a first contrast-agent distribution, and to generate, by way of material decomposition, a second virtual non-contrast X-ray image on the basis of second raw X-ray data, which is associated with a second contrast-agent distribution. The non-contrast images generated are transferred to a registration unit 33, which is also part of the motion correction device 30. The registration unit 33 registers the first virtual non-contrast X-ray image with the second virtual non-contrast X-ray image. The registration unit 33 determines a transformation field on the basis of the registration. Then using the determined transformation field, the registration unit 33 uses the data from the transformation field to register first X-ray image data, which is based on the first raw X-ray data, with second X-ray image data, which is based on the second raw X-ray data. The first X-ray image data has a different contrast distribution from that of the second X-ray image data. The first and second X-ray image data is generated by a reconstruction unit (not shown) and transferred to the registration unit 33 via the input interface 31.

The registration unit 33 transfers the registered image data to an output interface 34, which outputs the generated image data.

Figure 4:
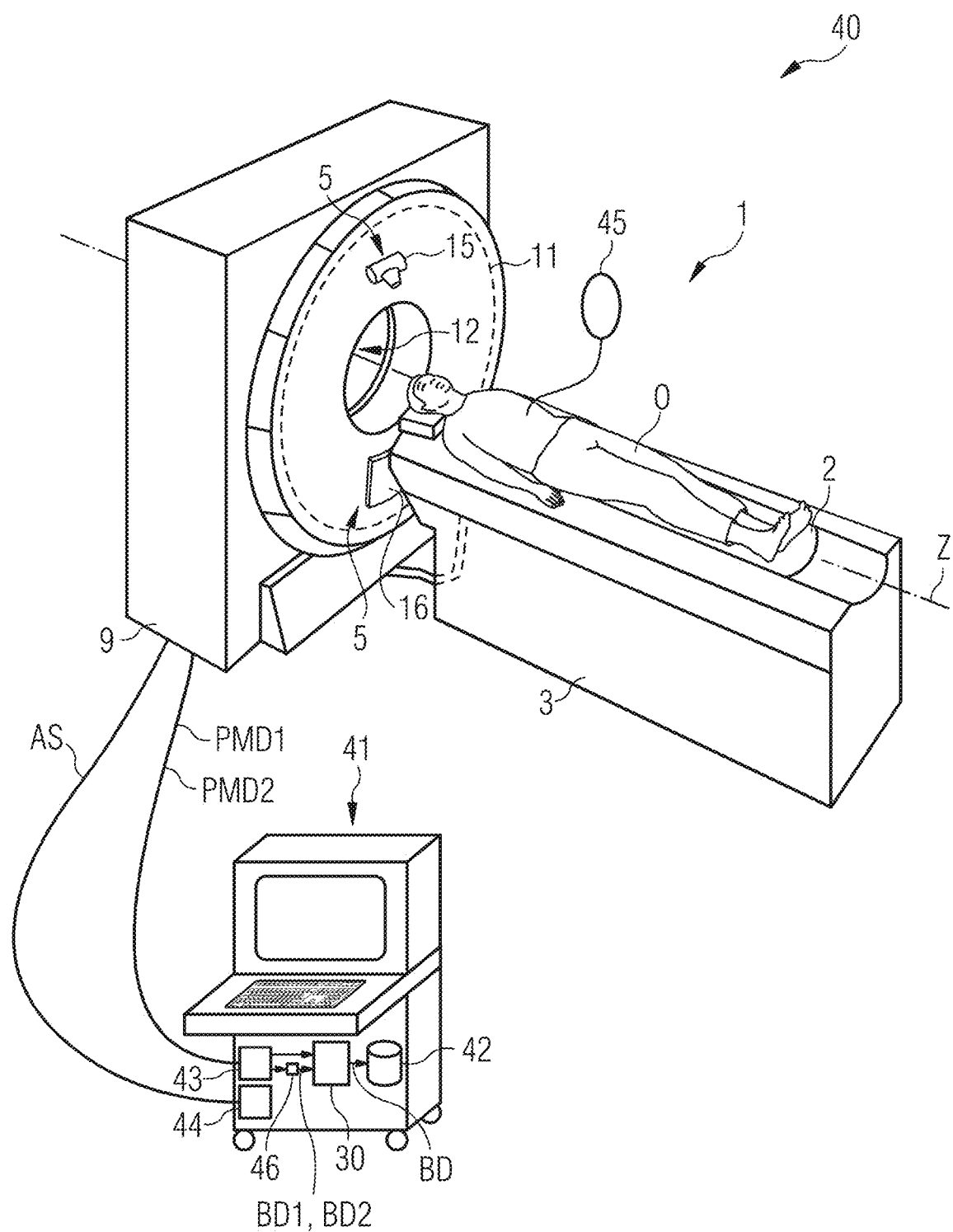
FIG. 4 shows a schematic diagram of a CT system according to an example embodiment of the invention.

FIG. 4 shows an X-ray imaging system, in this case a CT system 40, according to an example embodiment of the invention.

The CT system 40, which is in the form of a CT system having a photon-counting detector 16, includes primarily a standard scanner 9, in which, on a gantry 11, a projection measurement data acquisition-unit 5 comprising a photon-counting detector 16 and an X-ray source 15, which is located opposite the photon-counting detector 16, rotates about a measurement space 12. In front of the scanner 9 is a patient positioning device 3, or patient table 3, the upper part 2 of which, together with a patient O thereon, can be moved toward the scanner 9 in order to move the patient O through the measurement space 12 relative to the detector system 16. The scanner 9 and the patient table 3 are controlled by a controller 41, from which come acquisition control signals AS via a standard control interface 44 in order to control the entire system in accordance with specified measurement protocols in the usual way.

In the case of spiral acquisition, movement of the patient O along the z-direction, which corresponds to the system axis z lengthwise through the measurement space 12, and the simultaneous rotation of the X-ray source 15 result in a helical path for the X-ray source 15 relative to the patient O during the measurement. The detector 16 runs in parallel with this process always opposite the X-ray source 15 in order to capture spectrally resolved projection measurement data PMD1, PMD2, which is then used to reconstruct volume and/or slice image data. It is equally possible to perform a sequential measurement process in which travel is performed to a fixed position in the z-direction, and then during one revolution, part of a revolution or a plurality of revolutions at the z-position concerned, the required spectrally resolved projection measurement data PMD1, PMD2 is captured in order to reconstruct a sectional image at this z-position or to reconstruct image data from the projection measurement data at a plurality of z-positions.

In principle, the method according to an embodiment of the invention can also be applied to other CT systems, for instance comprising a plurality of X-ray sources or comprising a full-ring detector. For example, the method according to an embodiment of the invention can also be applied to a system comprising an immobile patient table and a gantry that moves in the z-direction (known as a sliding gantry).

The spectrally resolved projection measurement data PMD1, PMD2 (also referred to below as raw data) acquired by the detector 16 is passed to the controller 41 via a raw-data interface 43. This raw data is then processed, if applicable after suitable preprocessing, in a motion correction device 30, which in this example embodiment is implemented in the form of software on a processor in the controller 41. In addition, a reconstruction unit 46 also reconstructs or processes the raw data into image data BD1, BD2. The reconstructed image data BD1, BD2 is then likewise input to the motion correction device 30. The motion correction device 30 is designed as shown in FIG. 3 and generates mutually registered image data BD from the raw data PMD1, PMD2 acquired at different times.

The mutually registered image data BD generated by the motion correction device 30 is then stored in a memory 42 of the controller 41 and/or output in the usual manner on the screen of the controller 41. It can also be supplied via an interface (not shown in FIG. 4) to a network connected to the computed tomography system 40, for instance to a radiology information system (RIS), and stored in a mass storage device accessible there, or output as images on printers or filming stations connected there. Thus the data can be processed in any manner and then stored or output.

FIG. 4 also shows a contrast-agent injection device 45, which is used to inject the patient O with a contrast agent K in advance, i.e. before the CT imaging process starts. The computed tomography system 40 can then use the X-ray imaging method according to an embodiment of the invention to capture images of the regions through which the contrast agent K flows.

The components of the motion correction device 30 can be implemented mostly or entirely in the form of software elements on a suitable processor. In particular, the interfaces between these components can also be purely in the form of software. The only requirement is that suitable memory regions are accessible in which the data is stored temporarily in a suitable manner and can be retrieved and updated at any time.

Finally, it shall be reiterated that the method and devices described above are merely preferred example embodiments of the invention, and that the invention can be modified by a person skilled in the art without departing from the scope of the invention insofar as this is defined by the claims. It is mentioned for the sake of completeness that the use of the indefinite article "a" or "an" does not rule out the possibility of there also being more than one of the features concerned. Likewise, the term "unit" does not exclude the possibility that the unit consists of a plurality of components, which may also be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A motion correction method, comprising:
   determining, by way of material decomposition, a first virtual non-contrast X-ray image of a region under examination based upon first spectral raw X-ray data associated with a first contrast distribution;
   determining, by way of material decomposition, a second virtual non-contrast X-ray image of the region under examination based upon second spectral raw X-ray data associated with a second contrast distribution, the second contrast distribution differing from the first contrast distribution;
   registering the first virtual non-contrast X-ray image with the second virtual non-contrast X-ray image, to determine a transformation field between the first virtual non-contrast X-ray image and the second virtual non-contrast X-ray image; and
   registering, based upon the transformation field determined, first X-ray image data based on the first spectral raw X-ray data with second X-ray image data based on the second spectral raw X-ray data.

2. The method of claim 1, wherein the first contrast distribution differs from the second contrast distribution because of a different contrast-agent concentration distribution.

3. The method of claim 2, wherein the first contrast distribution differs from the second contrast distribution because different contrast agents are used for the first X-ray image data and the second X-ray image data.

4. An X-ray imaging method, comprising:
   performing a first spectral X-ray acquisition of a region under examination with a first contrast distribution;
   performing a second spectral X-ray acquisition of the region under examination with a second contrast distribution;
   performing the motion correction method of claim 2;
   generating mutually registered first image data and second image data based upon the motion correction performed.

5. The X-ray imaging method of claim 4, wherein the first spectral X-ray data is obtained based upon one of:
   photon-counting detection;
   dual-source CT;
   rapid kV-switching CT;
   dual-layer CT;
   sequential acquisitions using different X-ray tube voltages; or
   split-filter CT.

6. The X-ray imaging method of claim 4, wherein the X-ray imaging method is a CT imaging method.

7. The method of claim 1, wherein the first contrast distribution differs from the second contrast distribution because different contrast agents are used for the first X-ray image data and the second X-ray image data.

8. An X-ray imaging method, comprising:
   performing a first spectral X-ray acquisition of a region under examination with a first contrast distribution;
   performing a second spectral X-ray acquisition of the region under examination with a second contrast distribution;
   performing the motion correction method of claim 1;
   generating mutually registered first image data and second image data based upon the motion correction performed.

9. The X-ray imaging method of claim 8, wherein the first spectral X-ray data is obtained based upon one of:
   photon-counting detection;
   dual-source CT;
   rapid kV-switching CT;
   dual-layer CT;
   sequential acquisitions using different X-ray tube voltages; or
   split-filter CT.

10. The X-ray imaging method of claim 8, wherein the X-ray imaging method is a CT imaging method.

11. A non-transitory computer program product storing a computer program, directly loadable into a storage device of an X-ray imaging system, including program segments to perform the method of claim 8 when the computer program is executed in the X-ray imaging system.

12. A non-transitory computer-readable medium storing program segments, readable and executable by a processor to perform the method of claim 8 when the program segments are executed by the processor.

13. A non-transitory computer program product storing a computer program, directly loadable into a storage device of an X-ray imaging system, including program segments to perform the method of claim 1 when the computer program is executed in the X-ray imaging system.

14. A non-transitory computer-readable medium storing program segments, readable and executable by a processor to perform the method of claim 1 when the program segments are executed by the processor.

15. A motion correction device, comprising:
   a decomposition device to determine, via material decomposition, a first virtual non-contrast X-ray image based upon first raw X-ray data associated with a first contrast distribution, and to determine, via material decomposition, a second virtual non-contrast X-ray image based upon second raw X-ray data associated with a second contrast distribution; and
   a registration device to determine a transformation field by registering the first virtual non-contrast X-ray image with the second virtual non-contrast X-ray image, and, using the transformation field determined, to register first X-ray image data based on the first raw X-ray data, with second X-ray image data based on the second raw X-ray data.

16. An X-ray imaging system comprising the motion correction device of claim 15.

17. The X-ray imaging system of claim 16, wherein the X-ray imaging system is a CT imaging device.

18. A motion correction device, comprising:
at least one processor to
- determine, via material decomposition, a first virtual non-contrast X-ray image based upon first raw X-ray data associated with a first contrast distribution,
- determine, via material decomposition, a second virtual non-contrast X-ray image based upon second raw X-ray data associated with a second contrast distribution,
- determine a transformation field by registering the first virtual non-contrast X-ray image with the second virtual non-contrast X-ray image, and
- register, using the transformation field determined, first X-ray image data based on the first raw X-ray data, with second X-ray image data based on the second raw X-ray data.

19. An X-ray imaging system comprising the motion correction device of claim 18.

20. The X-ray imaging system of claim 19, wherein the X-ray imaging system is a CT imaging device.

* * * * *